US009179979B2

(12) United States Patent
Jinno

(10) Patent No.: US 9,179,979 B2
(45) Date of Patent: Nov. 10, 2015

(54) MEDICAL ROBOT SYSTEM

(75) Inventor: Makoto Jinno, Fujinomiya (JP)

(73) Assignee: Karl Storz GmbH & Co. KG (DE)

(*) Notice: Subject to any disclaimer, the term of this patent is extended or adjusted under 35 U.S.C. 154(b) by 175 days.

(21) Appl. No.: 13/071,967

(22) Filed: Mar. 25, 2011

(65) Prior Publication Data

US 2011/0245844 A1 Oct. 6, 2011

(30) Foreign Application Priority Data

Mar. 30, 2010 (JP) ................. 2010-077868

(51) Int. Cl.
*A61B 19/00* (2006.01)
*A61B 17/34* (2006.01)
*A61B 17/00* (2006.01)

(52) U.S. Cl.
CPC ......... *A61B 19/2203* (2013.01); *A61B 17/3423* (2013.01); *A61B 19/5212* (2013.01); *A61B 2017/00464* (2013.01); *A61B 2017/3445* (2013.01); *A61B 2019/2223* (2013.01); *A61B 2019/2242* (2013.01); *A61B 2019/2276* (2013.01); *A61B 2019/265* (2013.01)

(58) Field of Classification Search
CPC ................... A61B 19/5244; A61B 2019/5244; A61B 2019/5255; A61B 2019/5265; A61B 19/22; A61B 19/2203
USPC .......... 606/1, 129–130, 205, 45, 46; 600/101, 600/429; 128/898–899; 414/1–8; 700/245–264; 74/490.01, 490.05; 901/14–18, 27–28, 46–49
See application file for complete search history.

(56) References Cited

U.S. PATENT DOCUMENTS

| 4,762,455 | A | * | 8/1988 | Coughlan et al. .................. 414/4 |
| 5,247,608 | A | * | 9/1993 | Flemming et al. ............ 700/255 |
| 5,737,500 | A | * | 4/1998 | Seraji et al. .................... 700/251 |
| 5,792,135 | A | * | 8/1998 | Madhani et al. .................. 606/1 |
| 6,331,181 | B1 | | 12/2001 | Tierney et al. |
| 6,441,577 | B2 | * | 8/2002 | Blumenkranz et al. .. 318/568.11 |
| 6,459,926 | B1 | * | 10/2002 | Nowlin et al. ................ 600/429 |
| 6,470,236 | B2 | * | 10/2002 | Ohtsuki ........................ 700/247 |
| 2002/0082612 | A1 | * | 6/2002 | Moll et al. ..................... 606/130 |
| 2009/0082784 | A1 | * | 3/2009 | Meissner et al. .............. 606/130 |
| 2009/0326318 | A1 | * | 12/2009 | Tognaccini et al. ........... 600/104 |
| 2009/0326711 | A1 | * | 12/2009 | Chang et al. .................. 700/248 |

FOREIGN PATENT DOCUMENTS

JP 2003-061969 3/2003

* cited by examiner

*Primary Examiner* — Melanie Tyson
*Assistant Examiner* — Sidharth Kapoor
(74) *Attorney, Agent, or Firm* — Whitmyer IP Group LLC

(57) ABSTRACT

A medical robot system includes a forceps arm provided with a forceps manipulator and a camera arm provided with an endoscope. The forceps manipulator and the endoscope are inserted into a living body through a common insertion implement. The system further includes an operating unit that generates a control signal to control the forceps manipulator and the forceps arm, a forceps motion control unit that controls motions of the forceps manipulator and the forceps arm according to the control signal from the operating unit, an endoscope motion control unit that controls motions of the endoscope and the camera arm, and an interference avoiding unit that controls an interference avoiding motion of the camera arm to avoid interference between the camera arm and the forceps arm while a visual point of the endoscope is kept constant.

14 Claims, 18 Drawing Sheets

MEDICAL ROBOT SYSTEM

CROSS REFERENCE TO RELATED APPLICATION

This document claims priority of Japanese Application Number 2010-077868, filed Mar. 30, 2010, the entire contents of which are hereby incorporated by reference.

BACKGROUND OF THE INVENTION

1. Field of the Invention

The present invention relates to a medical robot system for performing laparoscopic surgery using a forceps manipulator provided on a forceps arm and an endoscope provided on a camera arm, which are inserted into a living body through a common trocar.

2. Description of the Related Art

In laparoscopic surgery (endoscopic surgical operation), a few small holes are bored in a patient's abdominal region, an endoscope (e.g., rigid scope) and a manipulator (or forceps) and the like are inserted, and an operator (surgeon) performs a surgical operation while watching an image from the endoscope on a monitor. Such laparoscopic surgery is less burdensome because no laparotomy is required, and the number of days required for the patient to spend before recovery from the surgical operation or release from the hospital is greatly reduced. Therefore, it is expected to be applied to an expanding range of fields.

A manipulator system includes a manipulator and a control unit configured to control the manipulator, as described in Japanese Patent Laid-open No. 2003-61969, for example. The manipulator includes an operating unit to be operated manually and a working unit detachably attached to the operating unit. The working unit has an elongated shaft and a distal-end working unit (also called an end effecter) provided at the distal end of the shaft. Motors that actuate the distal-end working unit through wires are provided in the operating unit. The wires are wrapped around pulleys on the proximal side. The control unit drives the motors provided in the operating unit, whereby the wires are circulatorily driven through the pulleys.

On the other hand, a medical robot system in which a medical manipulator (forceps manipulator) is actuated by a robot arm has been proposed (see, for example, U.S. Pat. No. 6,331,181). Such a medical robot system can be remotely controlled by a master arm and various motions can be performed under program control. The medical robot system is provided with a plurality of robot arms, which can be selectively operated according to the surgical procedure intended. For instance, two robot arms are each provided with a manipulator and a further robot arm is provided with an endoscope. A surgical procedure can be carried out using an operating unit and a console remotely located from the robot arms, while the operator views the surgical site on a monitor.

SUMMARY OF THE INVENTION

In the medical robot system as above-mentioned, the procedure is carried out with the manipulator and endoscope inserted in the body cavity through an insertion implement called trocar, for example. In this instance, for reducing patient invasiveness, a so-called single port access may be used wherein a plurality of instruments, for example, a total of three instruments including two manipulators and one endoscope, are simultaneously inserted via a single trocar.

In single port access, the plurality of instruments are concentrated into the single trocar. Therefore, particularly if those robot arms for moving the instruments which are moved on the extracorporeal side of the trocar interfere with each other, it would become difficult to bring the distal-end working units of the manipulators and the endoscope into desired positions and attitudes. More specifically, when, for example, the distal-end working unit of one manipulator takes a desired attitude, the relevant robot arm also moves correspondingly to the attitude. Then the robot arm may interfere with another robot arm, for example, the robot arm for moving the endoscope.

In view of this, it may be contemplated to move the endoscope-moving robot arm according to the movement of the manipulator-moving robot arms in such a manner as to avoid interference with the manipulator-moving robot arms. Where such an avoiding motion is effected simply, however, the visual point of the endoscope would be changed in a complicated manner, making it difficult for the operating surgeon to smoothly advance the procedure. In some cases, it may be possible for the surgeon to lose sight of the affected part.

The present invention has been made in consideration of the above-mentioned problem involved in the related art. Accordingly, it is an object of the present invention to provide a medical robot system in which interference between arms for moving instruments can be obviated while appropriately securing the user's field of view.

According to the present invention, there is provided a medical robot system for performing laparoscopic surgery by inserting a forceps manipulator, provided on a forceps arm, and an endoscope, provided on a camera arm, into a living body through a common insertion implement. The medical robot system includes: an operating unit by which at least the forceps manipulator and the forceps arm can be operated; a forceps motion control unit configured to control motions of the forceps manipulator and the forceps arm on the basis of an input to the operating unit; an endoscope motion control unit configured to control motions of the endoscope and the camera arm; and an interference avoiding motion control unit configured to control an interference avoiding motion of the camera arm relative to the forceps arm, with a visual point of the endoscope being kept constant.

According to such a configuration as just-mentioned, since the medical robot system is provided with the interference avoiding motion control unit configured to control an interference avoiding motion of the camera arm relative to the forceps arm, with the visual point of the endoscope being kept constant, interference between the camera arm and the forceps arm can be obviated while keeping constant the visual point of the endoscope. Therefore, notwithstanding the technique of performing laparoscopic surgery by inserting the forceps manipulator and the endoscope through the common insertion implement, the interference avoiding motion of the arm can be effected while appropriately maintaining the field of view of the user (surgeon).

In this case, the forceps motion control unit may be provided with a forceps arm-occupied region calculation unit configured to calculate the region occupied by the forceps arm, and the endoscope motion control unit may be provided with a camera arm-occupied region calculation unit configured to calculate the region occupied by the camera arm. Further, the medical robot system may have an interference risk determination unit configured to determine the risk of interference between the forceps arm and the camera arm, based on the results of calculation of the occupied regions by the forceps arm-occupied region calculation unit and the camera arm-occupied region calculation unit. In addition, the interference avoiding motion control unit may, when the risk of interference is determined to be positive by the interference risk determination unit, calculate a trajectory for an interference avoiding motion of the endoscope arm and, based on the thus calculated trajectory, the endoscope motion control unit may effect an interference avoiding motion of the camera arm. This ensures that, since the risk of interference is determined, as required, by the interference risk determination unit during the surgical operation, an interference avoiding motion can be appropriately carried out when there is a risk of interference.

The interference risk determination unit may determine the risk of interference between the forceps arm and the camera arm by the risk of interference between upper end portions of those arm members provided on the forceps arm and the camera arm which are provided coaxially with the insertion implement. Specifically, the upper portions of the arm members provided coaxially with the insertion implement are considered to be high in risk of inter-arm interference from the standpoint of the structure of robot arms; therefore, it is possible, by determination of risk of interference between the upper end portions, to alleviate the processing burden on the interference risk determination unit.

The camera arm may have a multiaxial joint mechanism having a redundant degree of freedom. This ensures that it is possible, by utilizing the redundant degree of freedom, to effect an interference avoiding motion of the camera arm while not substantially changing the attitude of the endoscope disposed in a body cavity. Accordingly, the visual point can be more securely prevented from being changed at the time of the interference avoiding motion.

In addition, the endoscope may have an attitude change axis at a part which is inserted through the insertion implement and disposed inside the living body. This ensures that such an operation as keeping constant the visual point during the interference avoiding motion can be carried out more easily. Particularly, even where a camera arm lacking a redundant degree of freedom is used, it is possible, by appropriate drive control on the attitude change axis, to achieve an interference avoiding motion with no change of the visual point.

In this case, the endoscope motion control unit may, at the time of effecting the interference avoiding motion of the camera arm, perform drive control on the attitude change axis with reference to an organ coordinate system set on a patient's organ or an offset coordinate system set with an offset from the organ, thereby keeping constant the visual point of the endoscope during the interference avoiding motion.

The medical robot system may have a visual point fixation switch for determining whether it is possible or impossible to keep constant the visual point of the endoscope, and the endoscope motion control unit may perform control to keep constant the visual point of the endoscope, during the interference avoiding motion of the camera arm relative to the forceps arm, only in the case where the visual point fixation switch determines that it is possible to keep constant the visual point of the endoscope. This makes it possible to flexibly cope with situations where an automatic interference avoiding motion is unnecessary, such as, for example, a situation where the operation of the endoscope and the camera arm is carried out by a person other than the operating staff for the forceps manipulator.

According to the present invention, a medical robot system is provided with an interference avoiding motion control unit configured to control an interference avoiding motion of a camera arm relative to a forceps arm while keeping constant the visual point of an endoscope. This makes it possible to avoid interference between the camera arm and the forceps arm, while keeping constant the visual point of the endoscope. Consequently, notwithstanding the use of a technique of performing laparoscopic surgery by inserting a forceps manipulator and an endoscope into a living body through a common insertion implement, an arm interference avoiding motion can be effected while appropriately securing the user's field of view.

DETAILED DESCRIPTION OF THE PREFERRED EMBODIMENTS

Referring to the accompanying drawings, a preferred embodiment of a medical robot system according to the present invention will be described below.

Figure 1:
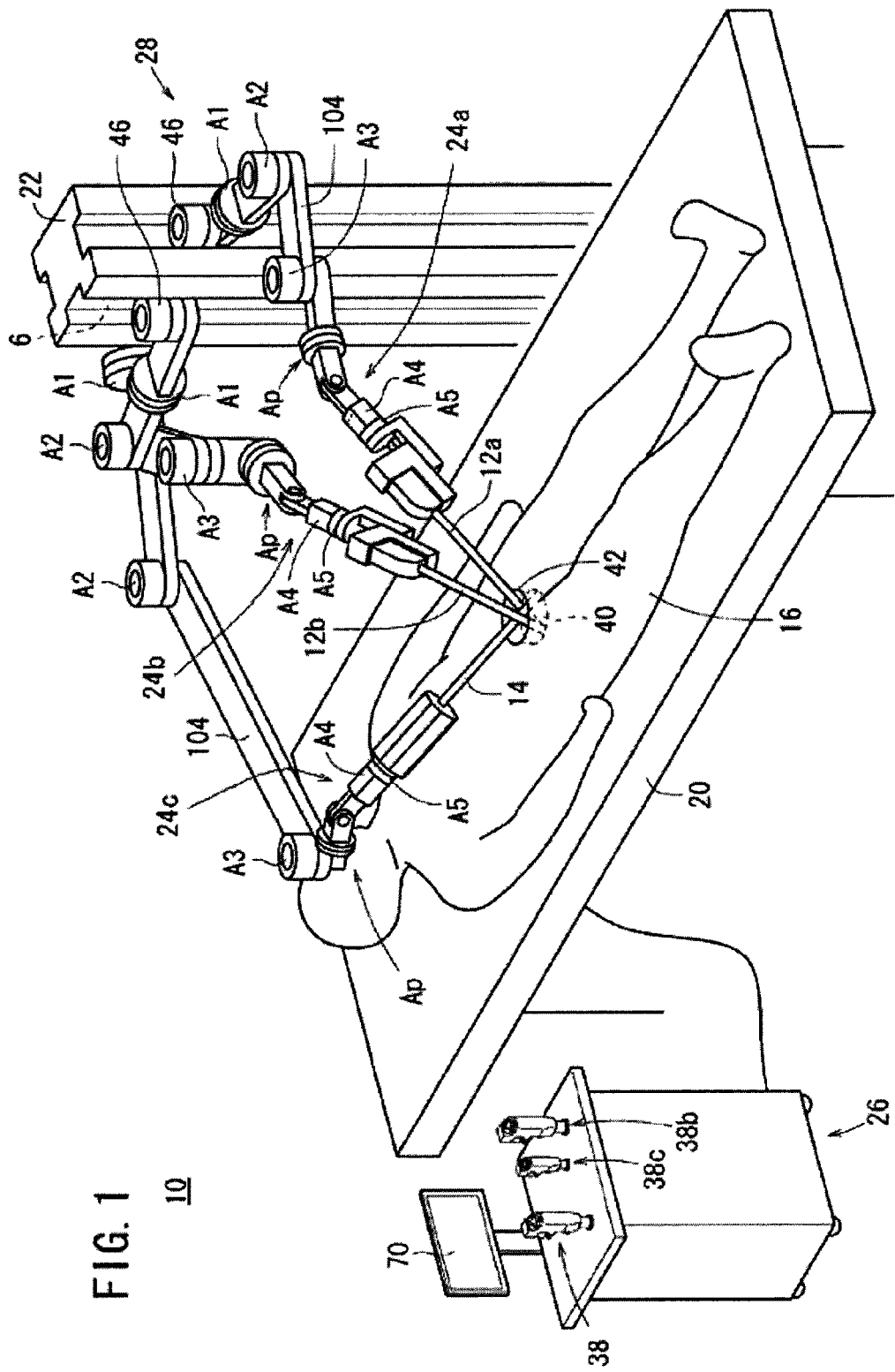
FIG. 1 is an overall configuration view of a medical robot system according to an embodiment of the present invention.

As shown in FIG. 1, a medical robot system 10 according to an embodiment of the invention performs a desired surgical treatment (laparoscopic surgery) on a patient 16 by use of a first forceps manipulator 12a, a second forceps manipulator 12b (hereinafter referred also to simply as "manipulator 12a" and "manipulator 12b") and an endoscope (camera) 14.

The medical robot system 10 includes a station 22 provided in the vicinity of an operating table 20 disposed in an operating room, three robot arms (FIG. 8) including a first forceps arm 24a, a second forceps arm 24b and a camera arm 24c (hereinafter referred also to simply as "arm 24a," "arm 24b" and "arm 24c") provided at the station 22, and a console (motion control unit) 26 for total control of these components. In short, the medical robot system 10 actuates an operating robot 28 having the arms 24a to 24c by use of the console 26, whereby a surgical procedure on the patient 16 can be carried out remotely.

The console 26 can send and receive information to and from the operating robot 28 by communication means such as wire, radio, a network or a combination thereof. The console 26 does not need to bear total control of the operating robot 28; for example, feedback control of the arms 24a to 24c may be provided on the robot side. The arms 24a to 24c may move under control of the console 26, and may perform automatic programmed motions, motions in response to joysticks, (operating units) 38a, 38b, 38c provided at the console 26, or composite motions of these motions.

The first and second forceps arms 24a and 24b have manipulators 12a and 12b at their distal ends, respectively, and the camera arm 24c has an endoscope 14 at its distal end. In the present embodiment, the manipulators 12a, 12b and the endoscope 14 are inserted into a body cavity 40 (the inside of a living body) through a trocar 42 which is a common insertion implement. Thus, the medical robot system 10 can perform procedures based on single port access wherein a plurality of instruments can be inserted into a living body through a single trocar 42. The manipulators 12a, 12b and the endoscope 14 can be detachably attached to the arms 24a to 24c, respectively.

The arms 24a to 24c each have a multiaxial joint mechanism, which is movably mounted on the station 22, and move up and down through a elevator mechanism 46. Under control of the console 26, the arms 24a to 24c can set the manipulators 12a, 12b and the endoscope 14 in arbitrary attitudes at arbitrary positions within respective ranges of motion.

Now, the manipulators 12a, 12b and the arms 24a, 24b will be described below.

The manipulators 12a, 12b respectively provided on the arms 24a, 24b are mainly for applying direct procedures to an affected part of the living body. At the distal end of each of the manipulators 12a, 12b, there is provided, for example, a gripper, a pair of scissors, an electrosurgical knife or the like. A retractor for retracting an organ or the like in the body cavity 40 to a predetermined place so as to secure a broad field of operation may be also provided at the distal end of the manipulators 12a and 12b. In the present embodiment, the manipulators 12a and 12b are substantially the same in configuration. Therefore, the configuration of the first forceps manipulator 12a and the configuration of a connecting part between the first forceps manipulator 12a and the first forceps arm 24a will be representatively described below, and detailed description of the second forceps manipulator 12b will be omitted.

Figure 2:
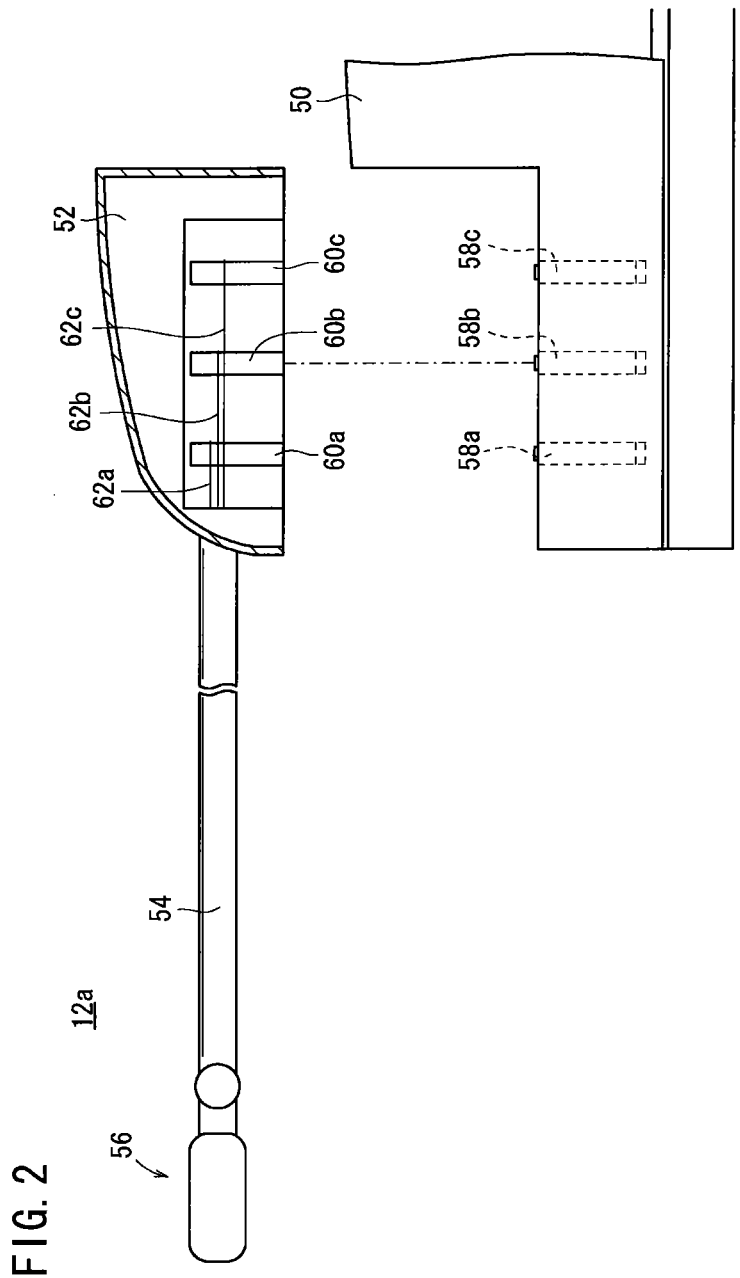
FIG. 2 is a partly omitted sectional plan view of a forceps manipulator.

As shown in FIG. 2, the manipulator 12a can be attached to and detached from a support member 50 provided at the distal end of the arm 24a. The support member 50 is equipped with three motors 58a to 58c which are arrayed along the Z-direction. The manipulator 12a includes a connecting block 52 for connection to the support member 50, a hollow joint shaft 54 extending in a distal direction from the connecting block 52, and a distal-end working unit 56 provided at the distal end of the joint shaft 54.

The connecting block 52 can be attached to and detached from the support member 50 through a predetermined attaching/detaching mechanism, and can be replaced. The connecting block 52 is provided therein with pulleys 60a to 60c to be engaged with the motors 58a to 58c, the pulleys 60a to 60c being arrayed correspondingly to the motors 58a to 58c. The motors 58a to 58c and the pulleys 60a to 60c are so configured that noncircular-shaped projections are provided on one of them, and corresponding-shaped recesses for engagement with the projections are provided on the other of them, whereby rotations of the motors 58a to 58c are transmitted respectively to the pulleys 60a to 60c through the engagement.

Wires 62a to 62c are wrapped around the pulleys 60a to 60c. The wires 62a to 62c are composed of flexible members and in a looped form. The wires 62a to 62c are partly fixed to the pulleys 60a to 60c for an anti-slipping purpose. Besides, the wires 62a to 62c are wrapped, for example, 1.5 turns around the pulleys 60a to 60c, and are extending through the inside of the joint shaft 54. As the pulleys 60a to 60c rotate, one of the two wires extending in the left or right direction is taken up, while the other is paid out.

The joint shaft 54 extends in the distal direction from the connecting block 52, and is provided with the distal-end working unit 56 at the distal end thereof. The joint shaft 54 may be provided at its intermediate portion with a joint part (not shown) for permitting bending thereat. This ensures that, during a procedure inside the body cavity 40, the manipulator 12a can be used as a retractor more effectively. This is because the manipulator 12a can push a desired organ while effectively avoiding interference with the other manipulator 12b and organs, and the like.

Figure 3:
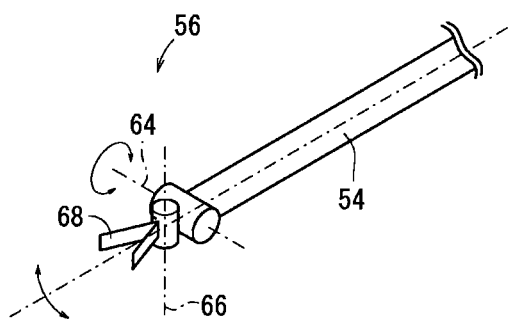
FIG. 3 is a perspective view for illustrating the structure of a distal-end working unit of the forceps manipulator.

As shown in FIG. 3, the distal-end working unit 56 is provided at the distal end of the joint shaft 54, and includes at least three pulleys (not shown) around which the wires 62a to 62C are wrapped respectively. As the wires 62a to 62c are moved back and forth by rotation of the pulleys 60a to 60c in the connecting block 52, the pulleys (not shown) in the distal-end working unit 56 are caused to rotate, whereby the distal-end working unit 56 can be moved in three axes. These motions are, for example, tilting motions about a pitch axis (joint axis) 64 and about a yaw axis (joint axis) 66, and opening/closing motions of a gripper 68. The distal-end working unit 56 may be provided with a rotating motion about a roll axis extending in the axial direction of the joint shaft 54, in addition to the motions about the just-mentioned axes or in place of the motions.

Now, the endoscope 14 and the camera arm 24c will be described below.

The endoscope 14 provided at the distal end of the camera arm 24c is a camera that picks up an image of the condition in the body cavity 40, and the image (picture) is displayed on a monitor 70 at the console 26. This permits the surgical operation staff (surgeon) to operate the manipulators 12a, 12b while observing the condition inside the body cavity 40, thereby performing a desired procedure on the affected part. The endoscope 14 can be attached to and detached from a support member at the distal end of the camera arm 24c, in substantially the same manner as the manipulator 12a shown in FIG. 2.

Figure 4:
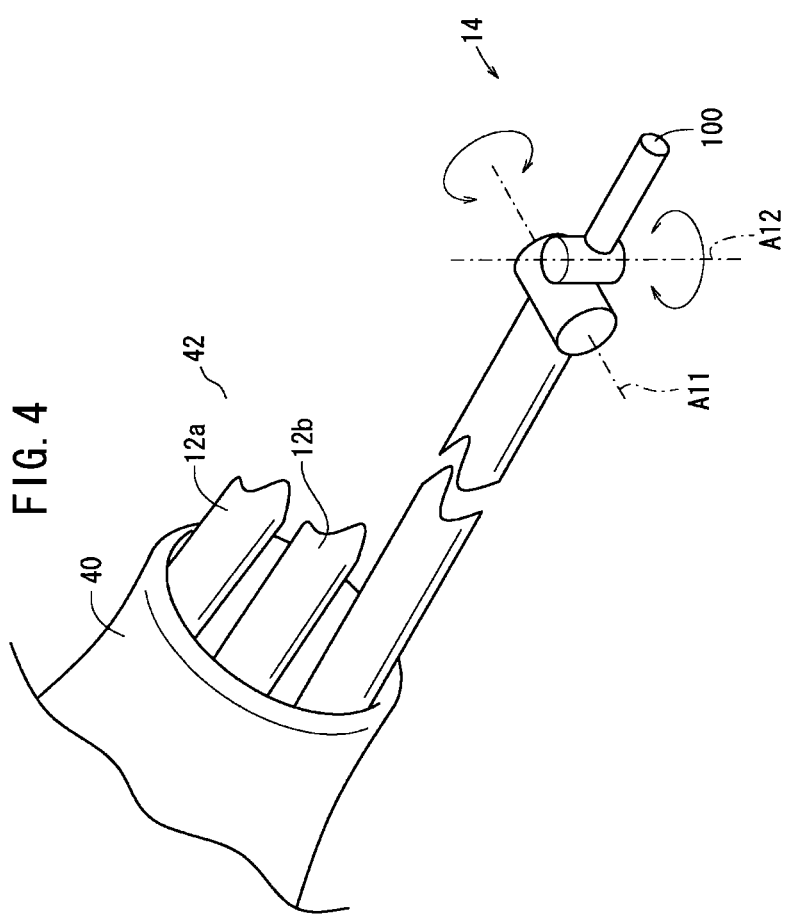
FIG. 4 is a perspective view for illustrating an attitude drive mechanism of an endoscope.

As shown in FIG. 4, the endoscope 14 is provided, for example, with a first attitude rotational axis (attitude change axis) A11 serving as a tilting axis (pitch axis) and a second attitude rotational axis (attitude change axis) A12 serving as a tilting axis (yaw axis), and can be put into biaxial motion inside the body cavity 40 by a drive mechanism using motors, wires and the like (not shown). This ensures that a lens part 100 at the distal end of the endoscope 14 can be put in a desired attitude, whereby a desired visual field having a visual point determined by the position and attitude of the lens 100 can be obtained.

Figure 5:
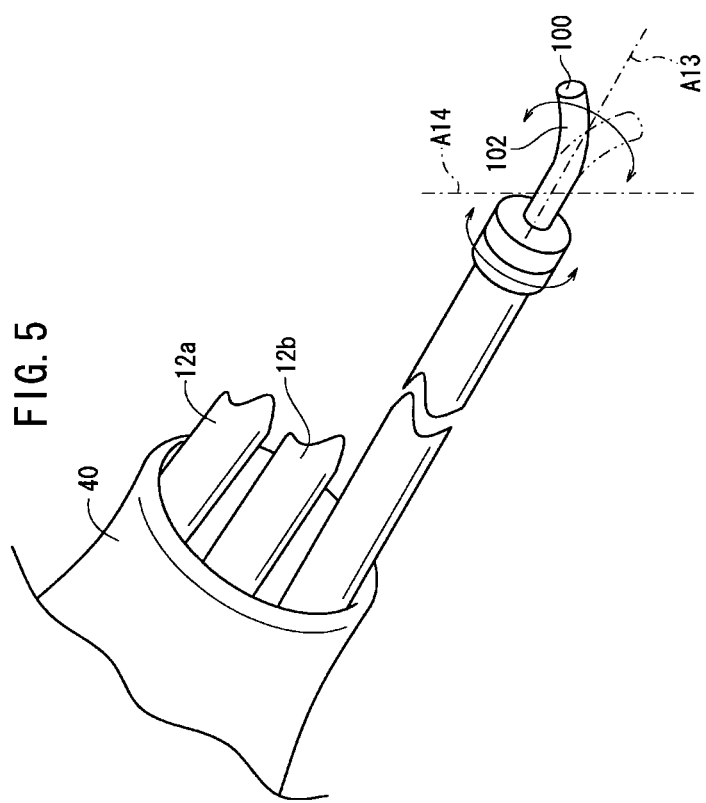
FIG. 5 is a perspective view for illustrating an attitude drive mechanism of an endoscope according to a modification.

Incidentally, the attitude axes (attitude change axis) for changing the attitude of the endoscope 14 inside the body cavity 40 may be other than those shown in FIG. 4. For example, a configuration as shown in FIG. 5 may be adopted in which a third attitude rotational axis (attitude change axis) A13 serving as a rotational axis (roll axis) and a fourth attitude rotational axis (attitude change axis) A14 serving as a tilting axis (pitch axis) are provided by use of drive mechanisms (not shown), and a distal-end curved part 102 provided at the distal end thereof with the lens part 100 is put in a desired attitude, whereby a desired visual field can be obtained. The distal-end curved part 102 may be configured, for example, in a bellows-like shape by arraying a plurality of node-like rings (not shown) therein, whereby the distal-end curved part 102 can be moved in two attitude axes. The attitude axes of the endoscope 14 may be a combination of not less than two of the first to fourth attitude rotational axes A11 to A14, or a combination thereof with one or more other axes.

Now, the configuration of the first and second forceps arms 24a, 24b and the camera arm 24c will be described below.

As above-mentioned, the arms 24a to 24c are members by which the manipulators 12a, 12b and the endoscope 14 are each moved into a desired position and into a desired attitude. Since the arms 24a to 24c are substantially the same in configuration, the configuration of the camera arm 24c equipped with the endoscope 14 will be representatively described below, and detailed descriptions of the first and second forceps arms 24a and 24b will be omitted.

Figure 6:
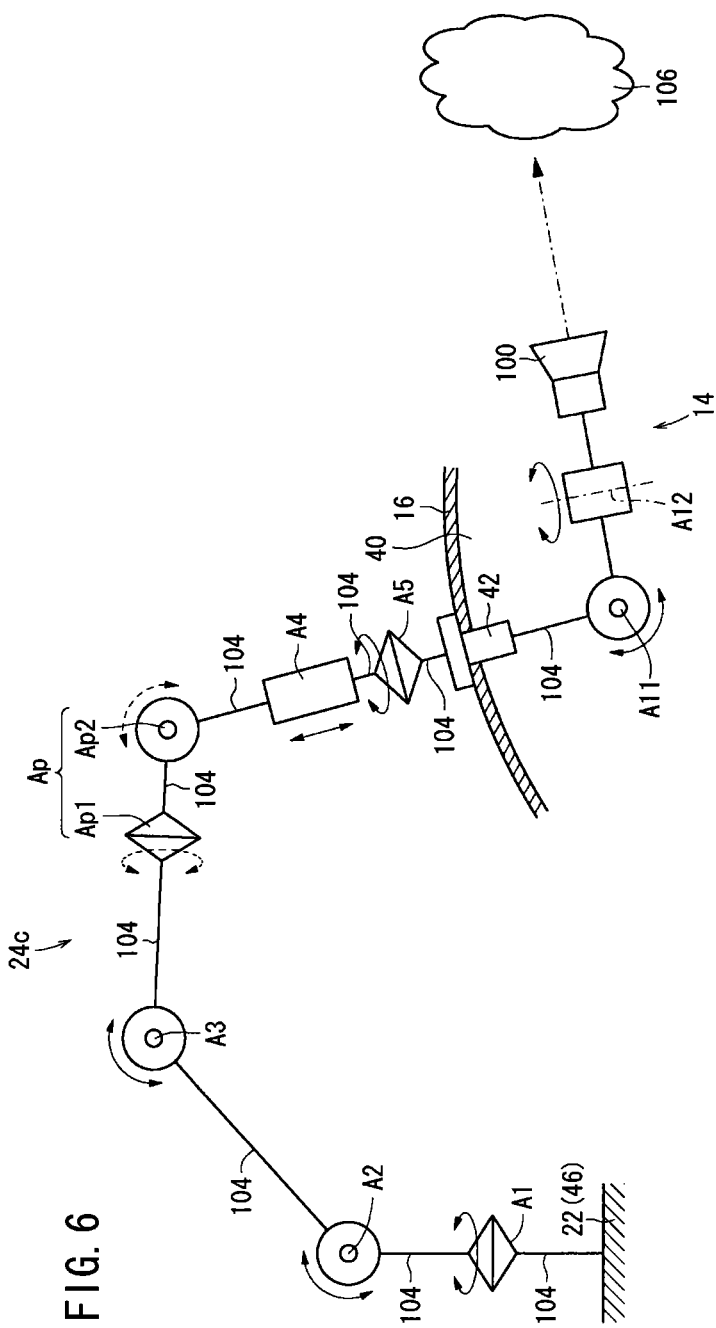
FIG. 6 is a schematic illustration of the structures of drive shafts of a camera arm and attitude axes of an endoscope provided at the distal end of the camera arm.

FIG. 6 schematically illustrates the structures of drive shafts of the camera arm 24c and the attitude axes of the endoscope 14 provided at the distal end of the camera arm 24c. Reference symbol 106 in FIG. 6 denotes an affected part (organ) as an object of treatment by the medical robot system 10.

As shown in FIGS. 1 and 6, the camera arm 24c has its proximal end mounted to the station 22 through the elevator mechanism 46, and is provided with a first axis (first rotational axis) A1, a second axis (second rotational axis) A2, a third axis (third rotational axis) A3, a passive axis (passive rotational axis) Ap, a fourth axis (translation axis) A4, and a fifth axis (fifth rotational axis) A5 in this order from the proximal side toward the distal side, with the axes being interconnected by arm members 104. The first to fifth axes A1 to A5 are drive shafts which are mounted on drive sources such as motors (not shown). On the other hand, the passive axis Ap is a passive axis with no drive shaft mounted thereon, and is composed of a first passive axis part Ap1 and a second passive axis part Ap2.

As seen from FIG. 6, the first axis A1, the fifth axis A5 and the first passive axis part Ap1 are rotational axes for rolling motion about the respective axis, whereas the second axis A2, the third axis A3 and the second passive axis Ap2 are tilting axes (turning axes) for pitching (yawing) motion in a direction intersecting the axial direction, and the fourth axis A4 is a translation axis for expanding/contracting motion in the axial direction.

The arm member 104 on the distal side of the fifth axis A5 is equipped with the endoscope 14. The endoscope 14 has the above-mentioned first attitude rotational axis A11 and second attitude rotational axis A12, and is provided with the lens part 100 at the distal end thereof.

Thus, the axis structure of the camera arm 24c and the endoscope 14 is a multiaxial joint mechanism composed of five-axial mechanism (five degrees of freedom) offered by the first to fifth axes A1 to A5, a biaxial mechanism (two degrees of freedom) offered by the first and second passive axis parts Ap1, Ap2, and a biaxial mechanism (two degrees of freedom) offered by the first and second attitude rotational axes A11, A12. Specifically, the camera arm 24c having a total of seven degrees of freedom is configured as a redundant arm provided with a redundant degree of freedom by the fourth axis A4. Incidentally, in the camera arm 24c, the fifth axis A5, for example, may be omitted; in that case, also, the camera arm 24c has the redundant degree of freedom and has a total of six degrees of freedom.

Now, the configuration of the console 26 will be described below.

Figure 7:
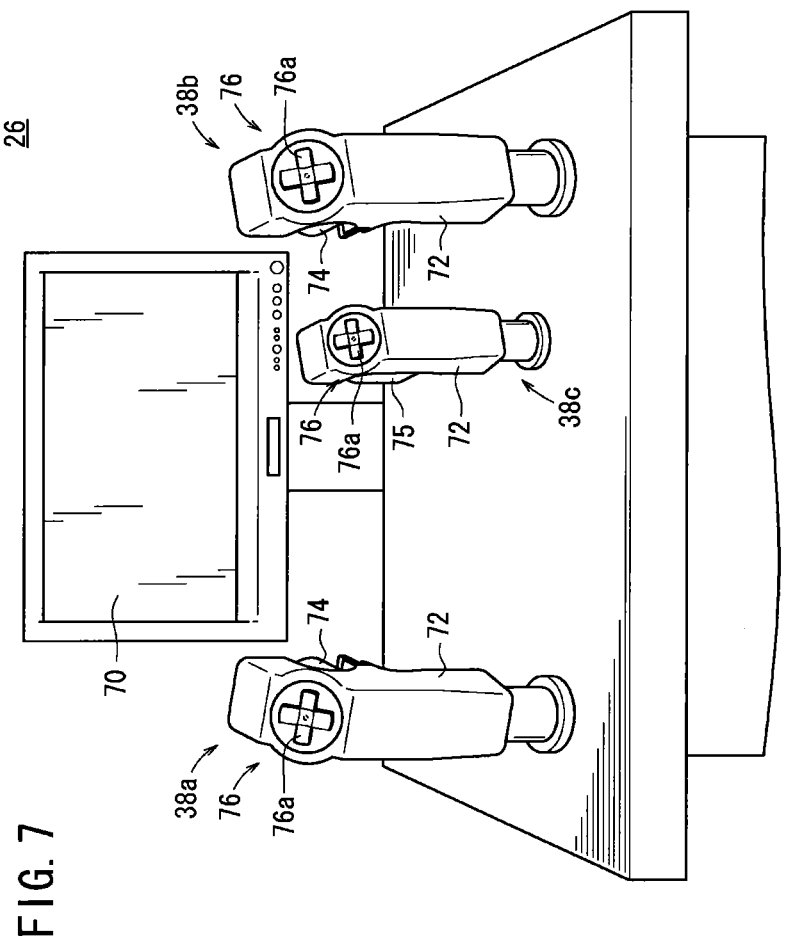
FIG. 7 is a front view of an operating unit provided on a console.

As shown in FIG. 7, the console 26 is provided with the three joysticks 38a, 38b, 38c as operating units (input units) to be operated manually, and with the monitor 70. An image captured by the endoscope 14 is displayed on the monitor 70.

By operating the left and right joysticks 38a and 38b, the arms 24a and 24b can be operated individually. By operating the central joystick 38c, the camera arm 24c can be operated. The arms 24a to 24c may be configured to be operated by other operating means which are not shown in the figure; besides, the joysticks 38a to 38c may be used by switching them over, as required. The joysticks 38a and 38b are provided at left and right positions such that they are easy to operate by both hands. The joysticks 38a and 38b may be master arms.

The joysticks 38a to 38c are each capable of up-down motions, twisting motions, and tilting motions in all directions, and the arms 24a to 24c are put into motions according to these motions of the joysticks 38a to 38c. The joysticks 38a to 38c are returned to the upright standard state shown in FIG. 7 when released.

The joysticks 38a and 38b are the same in structure, and each includes a hand grip 72 gripped by hand, a trigger lever 74 pushed and pulled mainly by an index finger or a middle finger, and a composite input unit 76 operated mainly by a thumb. By operating the trigger lever 74, for example, the gripper 68 of the manipulator 12a, 12b can be opened and closed. The composite input unit 76 is provided at its center with a cross-shaped seesaw-type switch 76a. By operating the seesaw-type switch 76a, tilting motions in the pitch axis 64 and the yaw axis 66 can be effected.

The joystick 38c may be basically the same in structure as the joysticks 38a, 38b. By operating the seesaw-type switch 76a at the composite input unit 76 of the joystick 38c, motions of the endoscope 14 in two attitude axes (A11, A12 or A13, A14) can be effected. In addition, the trigger lever 74 may be replaced by, for example, a visual point fixation switch 75 for determining whether it is possible or impossible to keep constant the visual point of the endoscope. Naturally, as an operating unit for the endoscope 14 and the camera arm 24c, devices other than the console 26 may be provided with the joystick 38c or a similar operating unit. The visual point fixation switch 75 is a switch which, under control of the console 26, performs automatic drive control on the first to fifth axes A1 to A5 of the camera arm 24c and the first and second rotational axes A11 and A12 of the endoscope 14, so as to maintain the visual point (or line of sight or visual field) relevant to the endoscope 14 at a fixed position (or a substantially fixed position), for example, on the affected part 106 (see FIG. 6), during an interference avoiding motion for avoiding interference between the camera arm 24c and any of the forceps arms 24a, 24b which will be described later.

Figure 8:
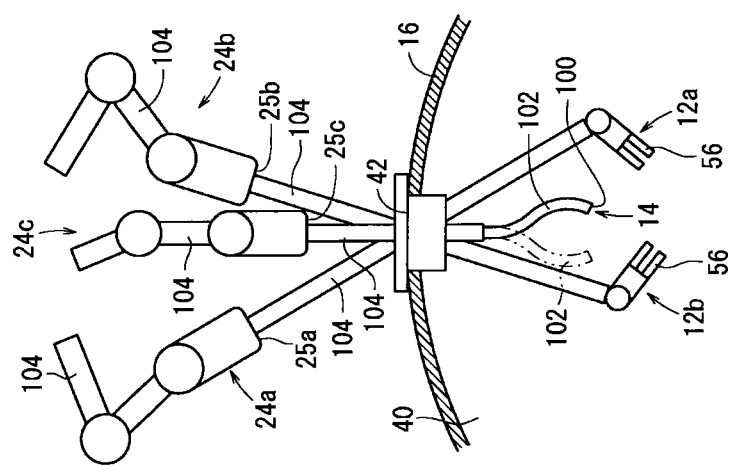
FIG. 8 schematically illustrates the states of forceps arms and the camera arm in a surgical operation based on single port access.

In the medical robot system 10 configured as above, as schematically illustrated in FIG. 8, a desired treatment of an affected part by the manipulators 12a and 12b is carried out while performing drive control on the arms 24a to 24c and imaging and visually checking the inside of a body cavity 40 by way of the endoscope 14.

Figures 9A, 9B:
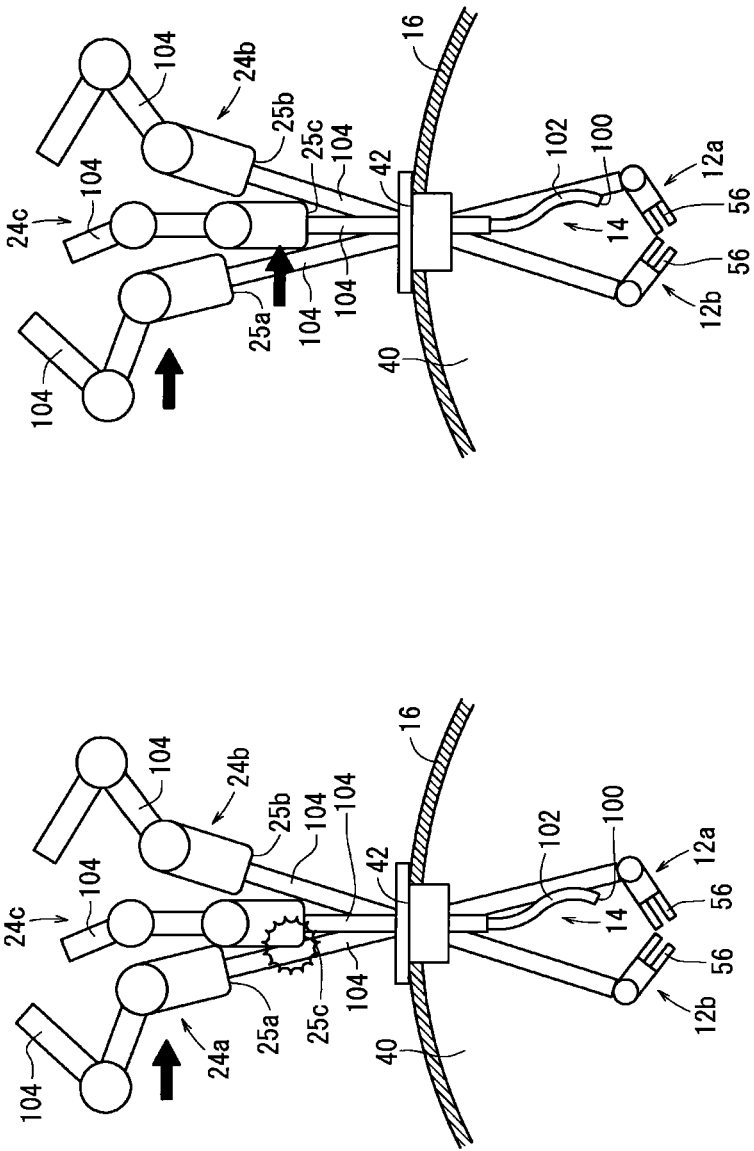
FIG. 9A schematically illustrates the state of interference between the forceps arm and the camera arm during the surgical operation based on single port access.
FIG. 9B schematically illustrates an interference avoiding motion of the camera arm during the surgical operation based on single port access.

In the medical robot system 10, however, a problem may arise as follows. Since the three instruments (the manipulators 12a, 12b and the endoscope 14) are inserted into the body cavity 40 through the single trocar 42, the arms 24a to 24c converge around the extracorporeal side of the trocar 42. Depending on the attitudes of the distal ends of the arms, therefore, the camera arm 24c may interfere with the first forceps arm 24a or the second forceps arm 24b. As a result, the visual point of the endoscope 14 may be shifted, or it may become difficult to move the distal-end working units 56 into desired attitudes. Particularly, arm upper end portions 25a, 25b, 25c (for example, in FIG. 6, joint parts of the arm members 104 extending upward from the trocar 42 to the fifth axis A5) of the arm members 104 provided approximately coaxially with the trocar 42 and the like are located near the trocar 42 and, therefore, they are liable to approach and interfere with each other. For instance, as shown in FIG. 9A, when the first forceps arm 24a is moved, its arm upper end portion 25a may interfere (make contact) with the arm upper end portion 25c of the camera arm 24c.

In view of this, in the medical robot system 10 according to the present embodiment, the console 26 is provided with a control function for avoiding interference of the camera arm 24c with the first and second forceps arms 24a, 24b while keeping constant the visual point or visual field of the endoscope 14, and drive control on the above-mentioned multi-axial joint mechanism (see FIG. 6) of the camera arm 24c (and the endoscope 14) is performed, as required. Consequently, such interference can be avoided, as shown in FIG. 9B.

Figure 10:
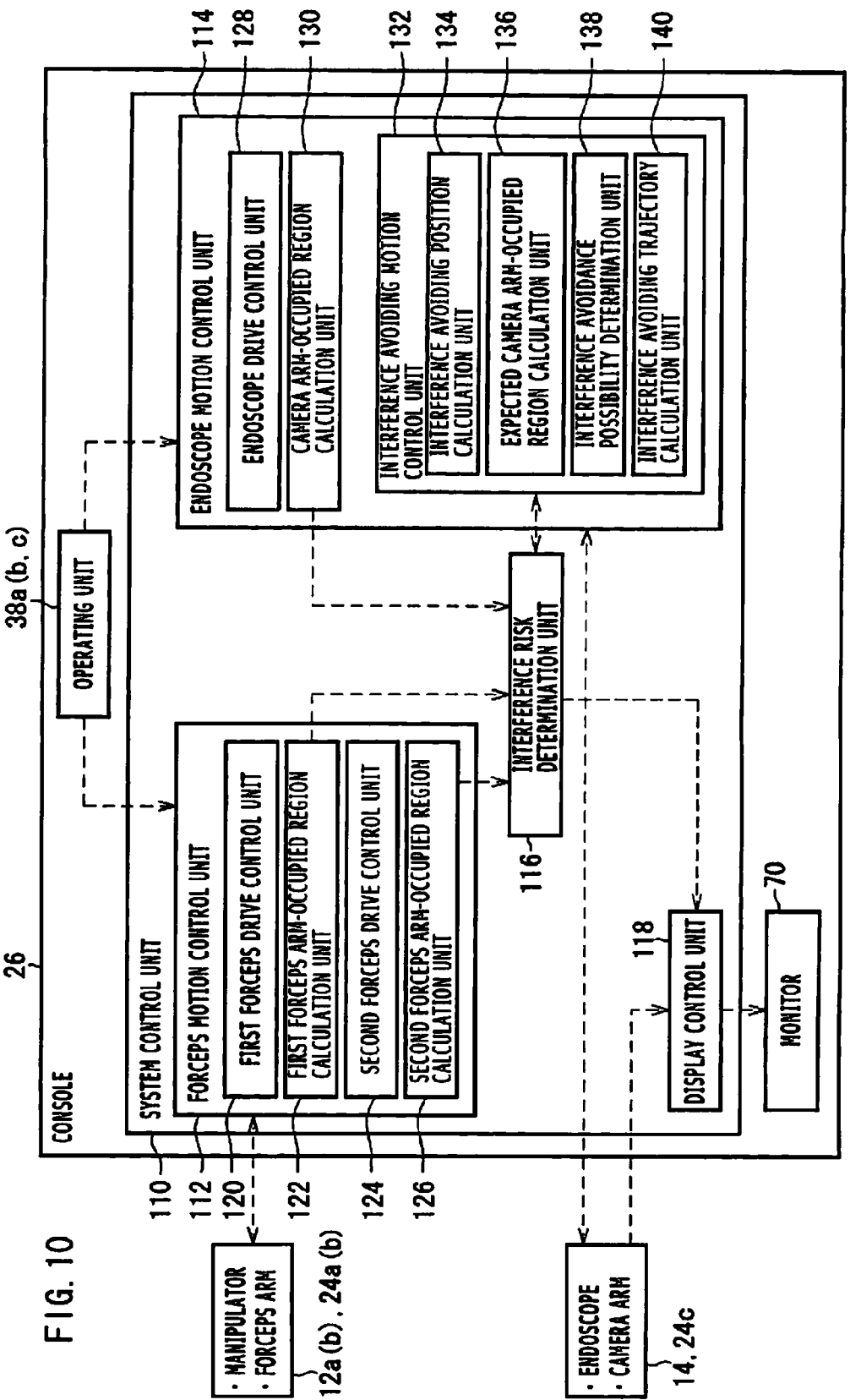
FIG. 10 is a block diagram of functions possessed by the console.

First, referring to FIG. 10, the control functions of the console 26 will be described. FIG. 10 is a block diagram of the functions of the console 26.

As shown in FIG. 10, the console 26 includes the joysticks 38a to 38c as operating units, the monitor 70, and a system control unit 110. The system control unit 110 is a total control unit for the console 26, in other words, the medical robot system 10, and includes a forceps motion control unit 112, an endoscope motion control unit 114, an interference risk determination unit 116, and a display control unit 118. It may be embodied by a programmable special purpose or general purpose electronic computer having a CPU and memory, or any other appropriate control device.

The forceps motion control unit 112 includes: a first forceps drive control unit 120 that controls the motions of the first forceps manipulator 12a and the first forceps arm 24a; a first forceps arm-occupied region calculation unit 122 that calculates (computes) the region occupied by the first forceps arm 24a (for example, as indicated by positional coordinates in a reference coordinate system used by the operating robot 28 which is set at the center of the station 22); a second forceps drive control unit 124 that controls the motions of the second forceps manipulator 12b and the second forceps arm 24b; and a second forceps arm-occupied region calculation unit 126 that calculates the region occupied by the second forceps arm 24b.

The endoscope motion control unit 114 includes: an endoscope drive control unit 128 that controls the motions of the endoscope 14 and the camera arm 24c; a camera arm-occupied region calculation unit 130 that calculates the region occupied by the camera arm 24c; and an interference avoiding motion calculation unit (interference avoiding motion control unit) 132 that performs processing necessary for an interference avoiding motion of the camera arm 24c relative to the first and second forceps arms 24a, 24b.

The interference risk determination unit 116 determines the risk of interference of the camera arm 24c with the first and second forceps arms 24a, 24b, based on the current positions (occupied regions) of the arms 24a to 24c which are obtained by the first and second forceps arm-occupied region calculation units 122, 126 and the camera arm-occupied region calculation unit 130.

Then, the interference avoiding motion calculation unit 132 provided in the endoscope motion control unit 114 includes: an interference avoiding position calculation unit 134 that calculates an interference avoiding position (coordinates) of the camera arm 24c when it is determined by the interference risk determination unit 116 that there is a risk of interference; and an expected camera arm-occupied region calculation unit 136 that calculates the region expected to be occupied by the camera arm 24c at the interference avoiding position (destination of avoidance) calculated by the interference avoiding position calculation unit 134. Furthermore, the interference avoiding motion calculation unit 132 includes: an interference avoidance possibility determination unit 138 that determines whether it is possible or impossible to avoid interference of the camera arm 24c with the first and second forceps arms 24a, 24b by moving the camera arm 24c into the expected occupied region calculated by the expected camera arm-occupied region calculation unit 136; and an interference avoiding trajectory calculation unit 140 that calculates a trajectory along which the camera arm 24c is to be moved to the interference avoiding position if the interference avoidance possibility determination unit 138 determines that it is possible to avoid interference.

Therefore, in the endoscope motion control unit 114, the camera arm 24c is moved under control of the endoscope drive control unit 128 along the trajectory calculated by the interference avoiding trajectory calculation unit 140, whereby an interference avoiding motion of the camera arm 24c relative to the first and second forceps arms 24a, 24b is performed.

The display control unit 118 is supplied with the image data picked up by the endoscope 14, arithmetically processes the image data, and displays a resultant image on the monitor 70. Incidentally, the display control unit 118 may have a function of displaying an alarm of danger of an interference, an alarm of an interference avoiding motion, or the like on the monitor 70, upon receiving various kinds of data from the interference risk determination unit 116 and the interference avoiding motion calculation unit 132, for example.

Now, the interference avoiding motion of the camera arm 24c relative to the first and second forceps arms 24a, 24b will be described below, referring to the flow charts shown in FIGS. 11A and 11B, which represent the control process sequence performed by the system control unit 110, for example as a result of the programming of a computer comprising an example of the system control unit 110.

First, a gas is fed into the vicinity of an affected part of the patient 16 to thereby secure the body cavity 40, and the endoscope 14 is inserted into the body cavity 40 through the trocar 42. While displaying the condition inside the body cavity 40 on the monitor 70, the distal-end working units 56 of the manipulators 12a and 12b are inserted through the same trocar 42 as that used for inserting the endoscope 14.

Next, the surgical operation staff (surgeon), while checking the condition inside the body cavity 40 which is obtained through the endoscope 14, operates the joysticks 38a, 38b so as to perform a desired laparoscopic surgical operation by the manipulators 12a, 12b provided at the distal ends of the arms 24a, 24b.

Figure 11B:
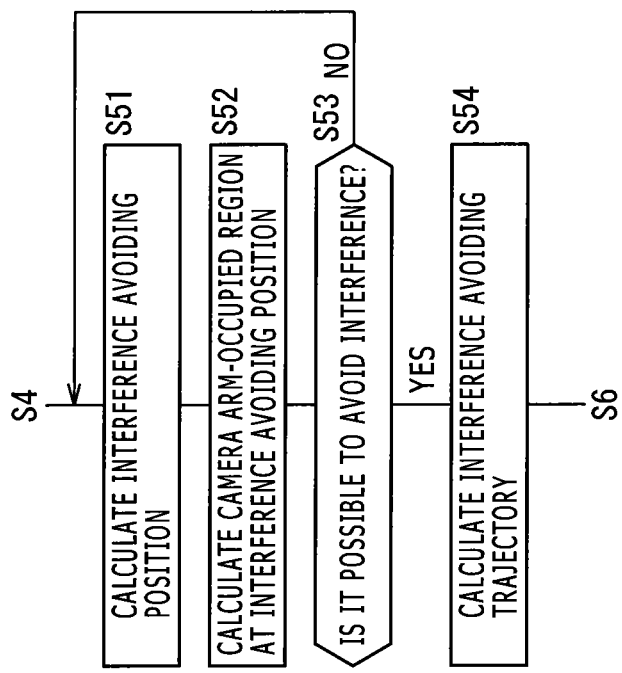
FIG. 11B is a flow chart for specific steps in a camera arm interference avoiding motion calculation step.
Figure 11A:
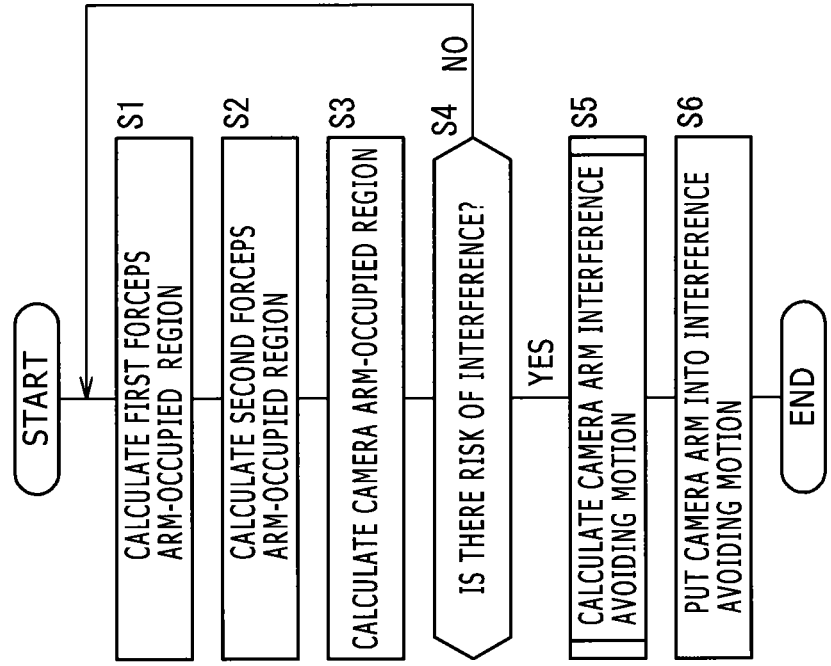
FIG. 11A is a flow chart for an operation flow pertaining to avoidance of interference of the camera arm with the forceps arm.

During such a surgical operation, the system control unit 110 at the console 26 first executes the steps shown in FIGS. 11A and 11B, including step S1 whereby the region occupied by the first forceps arm 24a driven under the control of the first forceps drive control unit 120 is calculated by the first forceps arm-occupied region calculation unit 122. In step S2, the region occupied by the second forceps arm 24b driven under the control of the second forceps drive control unit 124 is calculated by the second forceps arm-occupied region calculation unit 126. Substantially simultaneously, in step S3, the region occupied by the camera arm 24c driven under the control of the endoscope drive control unit 128 is calculated by the camera arm-occupied region calculation unit 130.

In this case, as the regions occupied by the arms 24a to 24c calculated by the arm-occupied region calculation units 122, 126, 130, the regions occupied by the whole bodies of the arms may be calculated. To reduce the processing load on the console 26 however, it may be sufficient to calculate only the regions occupied by those parts of the arms 24a to 24c which are likely to interfere with each other on a structural basis, such as the arm upper end portions 25a to 25c (see FIG. 8) of the arm members 104 right above the trocar 42.

In step S4, the interference risk determination unit 116, supplied with the results of calculations by the arm-occupied region calculation units 122, 126 and 130, determines whether or not either one or both of the distance between the first forceps arm 24a and the camera arm 24c, and the distance between the second forceps arm 24b and the camera arm 24c, are not more than a predetermined distance (the closest distance at which interference is obviated). The closest distance at which interference is obviated is here preferably set, for example, at a distance with some margin in consideration of control errors in the operating robot 28 and the like factors, in order that contact between the arm upper end portion 25a of the first forceps arm 24a and the arm upper end portion 25c of the camera arm 24c can be securely prevented.

If it is determined in step S4 that there is no risk of interference between the camera arm 24c and the first and second forceps arms 24a and 24b (the result of step S4 is NO), the control process returns to step S1, in which the calculation of the regions occupied by the arms 24a to 24c is started again.

On the other hand, if it is determined that there is a risk of interference between the camera arm 24c and the first and/or second forceps arms 24a, 24b (refer to the first forceps arm 24a indicated by the two-dotted chain line and the camera arm 24c indicated by the solid line in FIG. 12), that is, the result of step S4 is YES, step S5 is executed subsequently.

In step S5, the interference avoiding motion calculation unit 132 calculates an interference avoiding motion in the direction in which the camera arm 24c (arm upper end portion 25c) is spaced away from the first and/or second forceps arms 24a, 24b (arm upper end portions 25a, 25b).

More specifically, in step S5, first, in step S51 in FIG. 11B, the interference avoiding position calculation unit 134 calculates an interference avoiding position for the camera arm 24c. Next, in step S52, the expected camera arm-occupied region calculation unit 136 calculates the region expected to be occupied by the camera arm 24c located at the thus calculated interference avoiding position (see the camera arm 24c indicated by two-dotted chain line in FIG. 12).

In step S53, it is determined whether it is possible or impossible to avoid interference between the camera arm 24c and the first and second forceps arms 24a, 24b by moving the camera arm 24c into the interference avoiding position and the expectedly occupied region calculated in steps S51 and S52.

In the case where it is determined that the interference of the camera arm 24c with the first and second forceps arms 24a, 24b cannot be avoided even by moving the camera arm 24c into the interference avoiding position and the expectedly occupied region calculated in steps S51 and S52 (the result of step S53 is NO), the control process returns to step S51, in which calculation of another interference avoiding position and expectedly occupied region is carried out one more time.

On the other hand, in the case where it is determined that the interference of the camera arm 24c with the first and second forceps arms 24a, 24b can be avoided by moving the camera arm 24c into the interference avoiding position and the expectedly occupied region calculated in steps S51 and S52 (the result of step S53 is YES), step S54 is executed subsequently.

In step S54, the interference avoiding trajectory calculation unit 140 calculates a trajectory along which the camera arm 24c is to be moved from the current position thereof to the interference avoiding position calculated in step S51.

Then, in step S6 in FIG. 11A, according to the trajectory calculated in step S54 for movement of the camera arm 24c to the interference avoiding position, the camera arm 24c is driven under the control of the endoscope drive control unit 128, whereby an interference avoiding motion is effected. As a result, as the first forceps arm 24a and the camera arm 24c indicated by two-dotted chain lines in FIG. 12, the mutual interference of these arms can be avoided appropriately.

Figure 12:
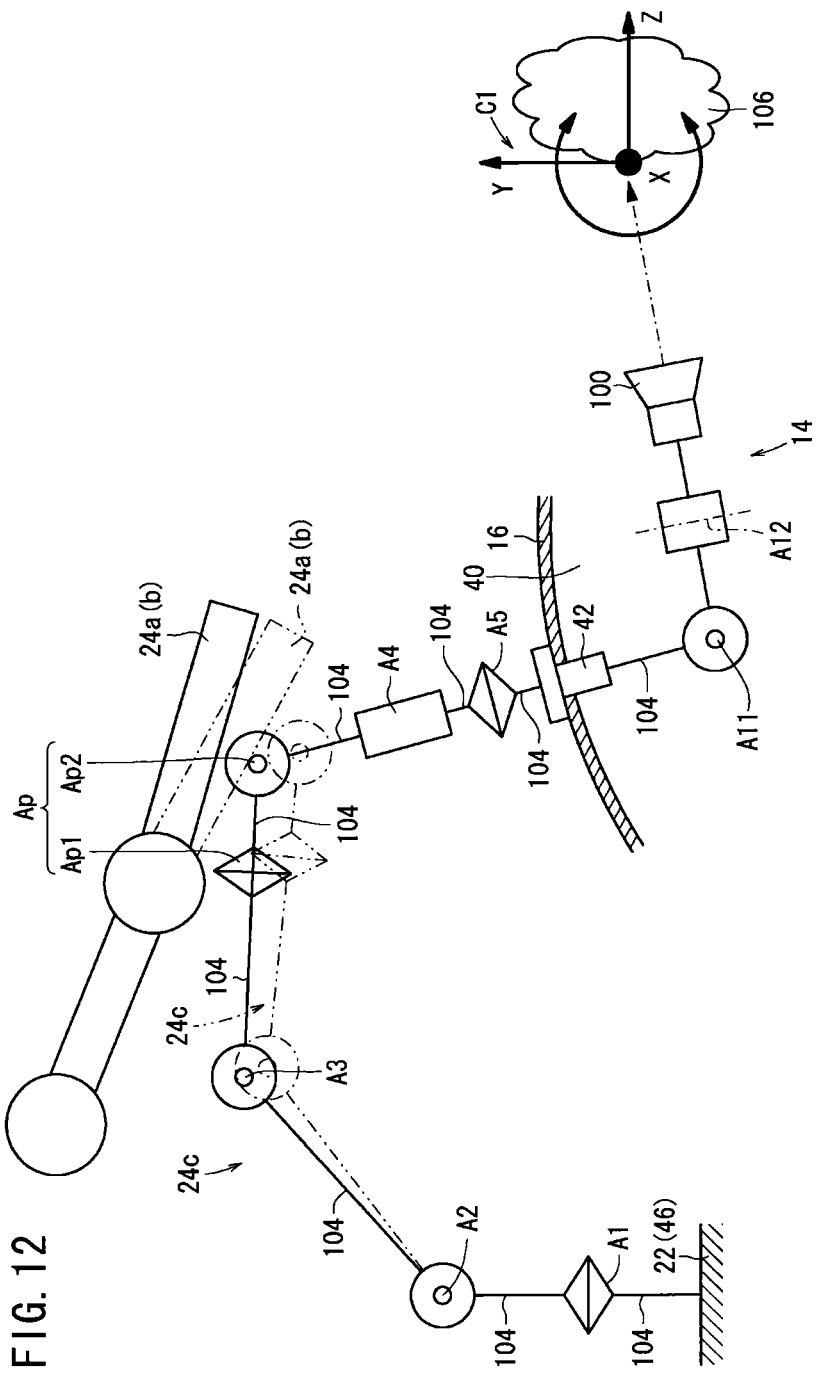
FIG. 12 illustrates an interference avoiding motion of the camera arm shown in FIG. 6.

In this instance, since the camera arm 24c includes a mechanism having a redundant degree of freedom (redundant arm axis of movement) in the present embodiment, the visual point (and visual field) of the endoscope 14 for the affected part 106 is not changed (or is little changed) by the interference avoiding motion, as shown in FIG. 12. Thus, in the medical robot system 10, interference among the arms 24a to 24c can be appropriately avoided, while appropriately securing the visual field for the surgical operation staff (surgeon), while preventing the visual point and the visual field from being changed.

A configuration may be adopted in which, for example, the interference avoiding motion conducted while keeping constant the visual point of the endoscope 14 by automatic drive control on the camera arm 24c is valid only when the above-mentioned visual point fixation switch 75 is ON and the interference avoiding motion is not carried out when the visual point fixation switch 75 is OFF. This makes it possible to flexibly cope with situations where an automatic interference avoiding motion is unnecessary, such as, for example, a situation where the operation of the joystick 38c as the operating unit for the endoscope 14 and the camera arm 24c is carried out by other staff than the surgical operation staff operating the manipulators 12a, 12b.

In the interference avoiding motion as described above, the attitude rotational axes A11 and A12 (alternatively A13 and A14) which are attitude axes of the endoscope 14 may be controlled so as to change the attitude with reference to, for example, an organ coordinate system C1 which is a Cartesian coordinate system having X-axis, Y-axis and Z-axis set on the affected part 106, as shown in FIG. 12. This ensures that motions can be effected while fixing the visual point for the affected part 106 (organ) even in the case where motions around the attitude rotational axes A11 and A12 are necessary to keep constant the visual point or the visual field of the endoscope 14 while moving the camera arm 24c through the interference avoiding motion. Naturally, as the reference coordinates for the attitude axes of the endoscope 14, other coordinate systems than the organ coordinate system C1 can also be used. For example, an offset coordinate system C2 set at a position offset from the affected part 106 (see FIG. 17) and the like may also be used.

In addition, the calculations of the interference avoiding position and the trajectory for movement in steps S51 to S54 mentioned above can be facilitated, for example, as follows. First, calculation is made to get the position of the arm upper end portion 25c of the camera arm 24c which is located right above the trocar 42, when it is rotated by predetermined angles about the X-axis, Y-axis and Z-axis in the above-mentioned coordinate system. Then, the relation of this position of the arm upper portion 25c with respect to the position of that arm upper portion 25a (25b) of the forceps arm 24a (24b), which is located right above the trocar 42 and determined to have a risk of interference is calculated. The camera arm 24c is put into an interference avoiding motion in the most efficient direction in accordance with the calculated relationship.

Incidentally, the interference avoiding motion according to the present embodiment can also be carried out by different types of arms than the camera arm 24c having the redundant degree of freedom shown in FIGS. 6 and 12. For example, the interference avoiding motion can be done by a camera arm 24d (see FIG. 13) or a camera arm 24e (see FIG. 14) which lack the redundant degree of freedom.

Figure 13:
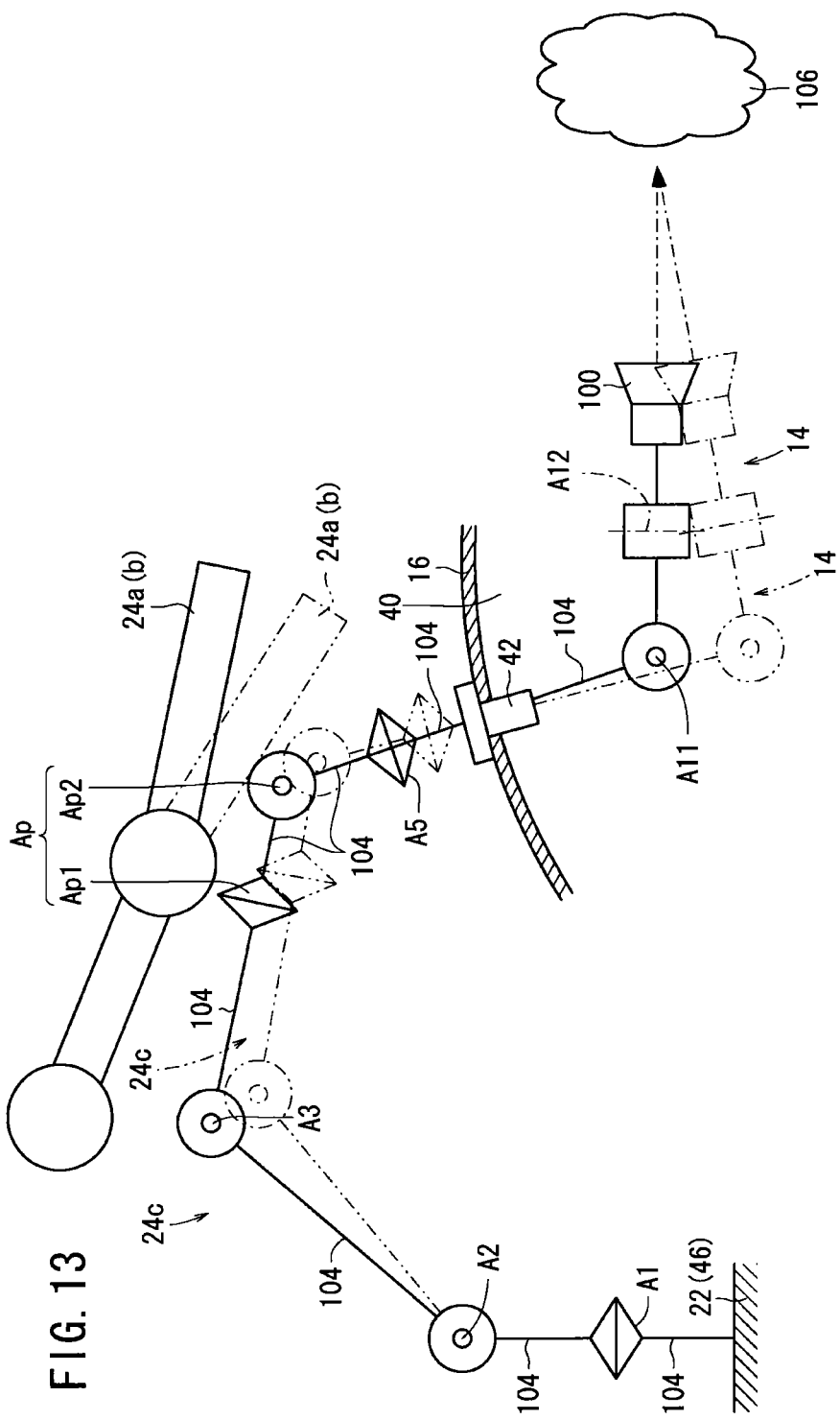
FIG. 13 schematically illustrates the structures of drive shafts of a camera arm and attitude axes of an endoscope provided at the distal end of the camera arm, according to a modification, as well as an interference avoiding motion thereof.
Figure 14:
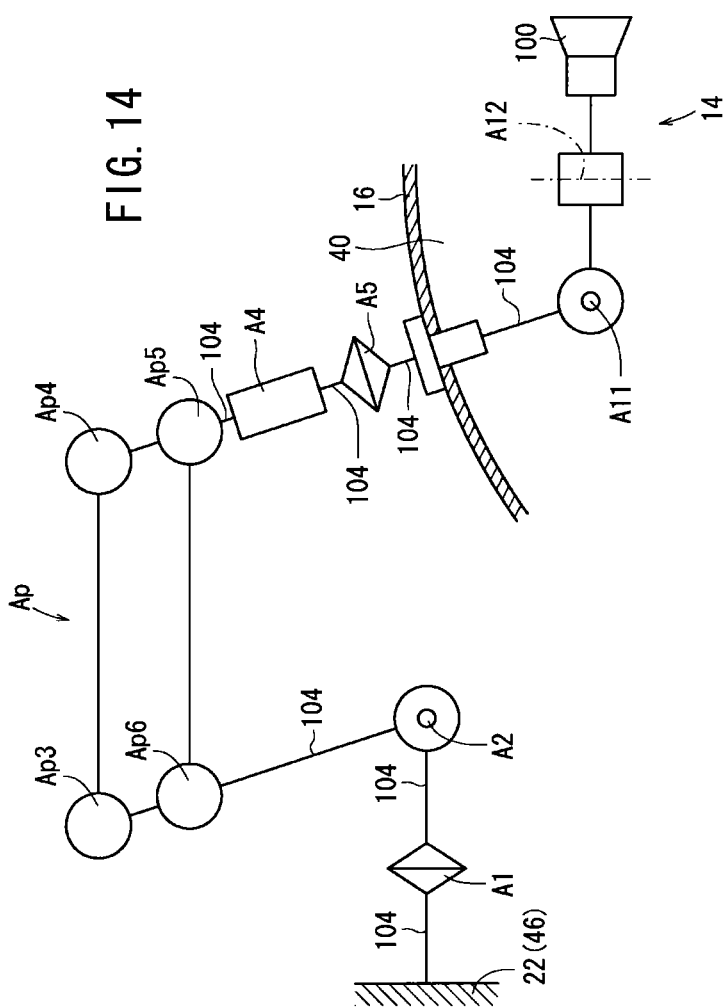
FIG. 14 schematically illustrates the structures of the drive shafts of the camera arm and the attitude axes of the endoscope provided at the distal end of the camera arm, according to a modification of the camera arm shown in FIG. 13.

As shown in FIG. 13, the camera arm 24d does not include the fourth axis A4, unlike the camera arm 24c (see FIG. 12). In addition, as shown in FIG. 14, the camera arm 24e has replaced the passive axis Ap in the camera arm 24d by parallel link arms Ap3, Ap4, Ap5, Ap6. Naturally, also in these camera arms 24d and 24e, the fifth axis A5, for example, may be omitted, as such omission is possible in the camera arm 24c.

In the camera arm 24d, for example, the fourth axis A4 which is a translation axis is omitted from the configuration of the camera arm 24c which would have more redundant degrees of freedom otherwise. Therefore, drive control must be also applied to the first attitude rotational axis A11 and the second attitude rotational axis A12 of the endoscope 14, in order to keep constant the visual point of the endoscope 14 for the affected part 106 during the interference avoiding motion, as indicated by two-dotted chain lines in FIG. 13.

In other words, in such a camera arm 24d (24e), line-of-view control using the attitude rotational axes A11, A12 (or A13, A14) which are attitude axes of the endoscope 14 is carried out appropriately, whereby the visual point of the endoscope 14 can be prevented from being changed.

Figure 15:
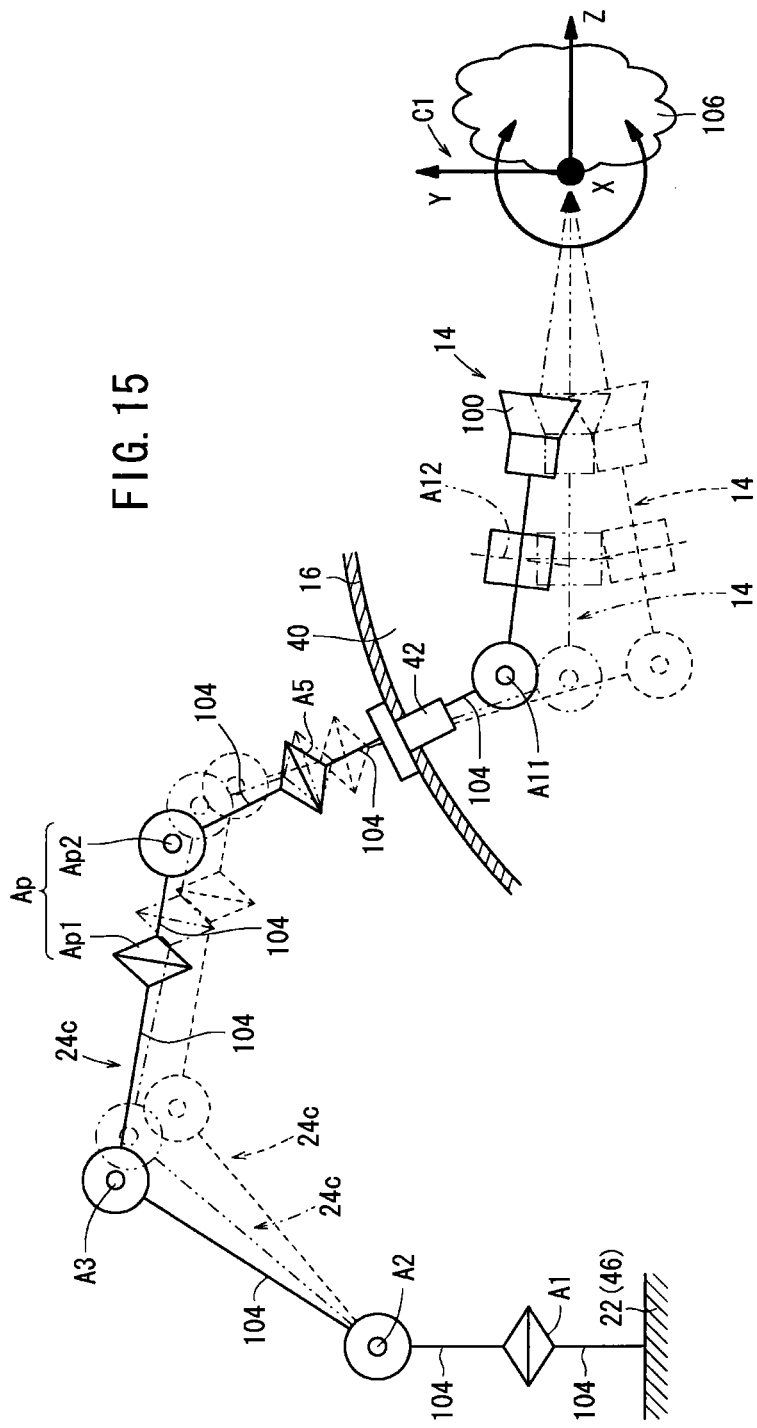
FIG. 15 illustrates an interference avoiding motion and a line-of-sight control in the case where an organ coordinate system is set, in the camera arm shown in FIG. 13.

As shown in FIG. 15, for example, a line-of-view of the lens part 100 may be guided by varying the attitude of the endoscope 14 with reference to the organ coordinate system C1 set on the affected part 106. This makes it possible to apply rotating motion or the like to the endoscope 14 without changing the visual point of the endoscope 14 with the origin of the organ coordinate system C1 as a center. Consequently, interference of the camera arm 24c can be appropriately obviated.

Figure 16:
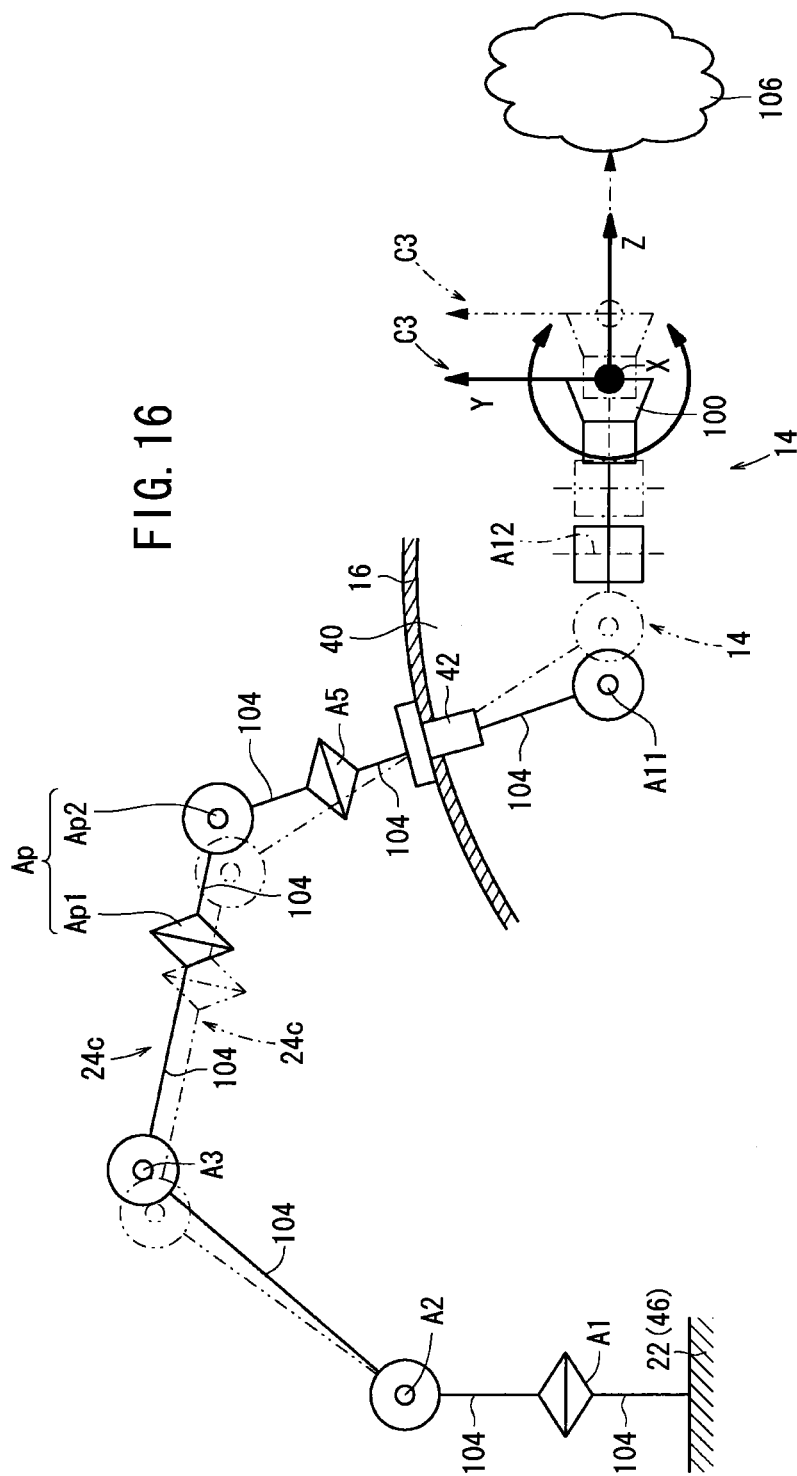
FIG. 16 illustrates an interference avoiding motion and a line-of-sight control in the case where a camera coordinate system is set, in the camera arm shown in FIG. 13.

As shown in FIG. 16, drive control may be conducted so as to change the attitude of the endoscope 14 with reference to a camera coordinate system C3 which is a Cartesian coordinate system having X-axis, Y-axis and Z-axis set on the lens part 100. This also makes it possible to appropriately avoid interference of the camera arm 24c without changing the visual point of the endoscope 14.

Figure 17:
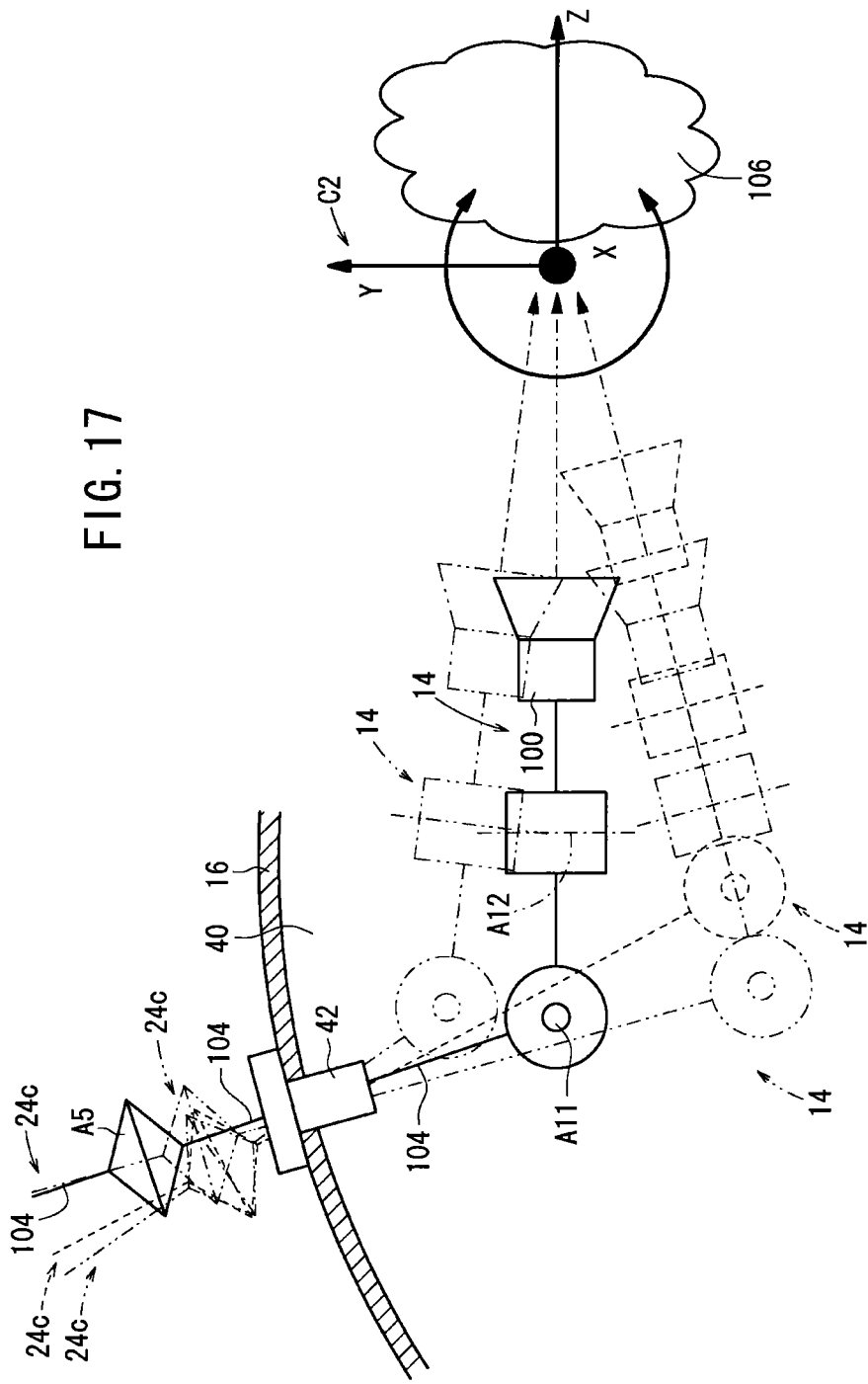
FIG. 17 is a major part enlarged illustration showing an interference avoiding motion and a line-of-sight control in the case where an offset coordinate system is set, in the camera arm shown in FIG. 13.

As shown in FIG. 17, drive control may be conducted so as to change the attitude of the endoscope 14 with reference to an offset coordinate system C2 which is a Cartesian coordinate system having X-axis, Y-axis and Z-axis set on a position offset from the affected part 106. In this case, the interference avoiding motion can be carried out while keeping constant the visual point of the endoscope 14 at a position a predetermined distance offset from the affected part 106. Therefore, the visual point can be preliminarily adjusted to a position in the vicinity of the distal end positions of the manipulators 12a, 12b located on the proximal side (the endoscope 14 side) relative to the affected part 106. This configuration can be used effectively, depending on the intended procedure.

Figure 18:
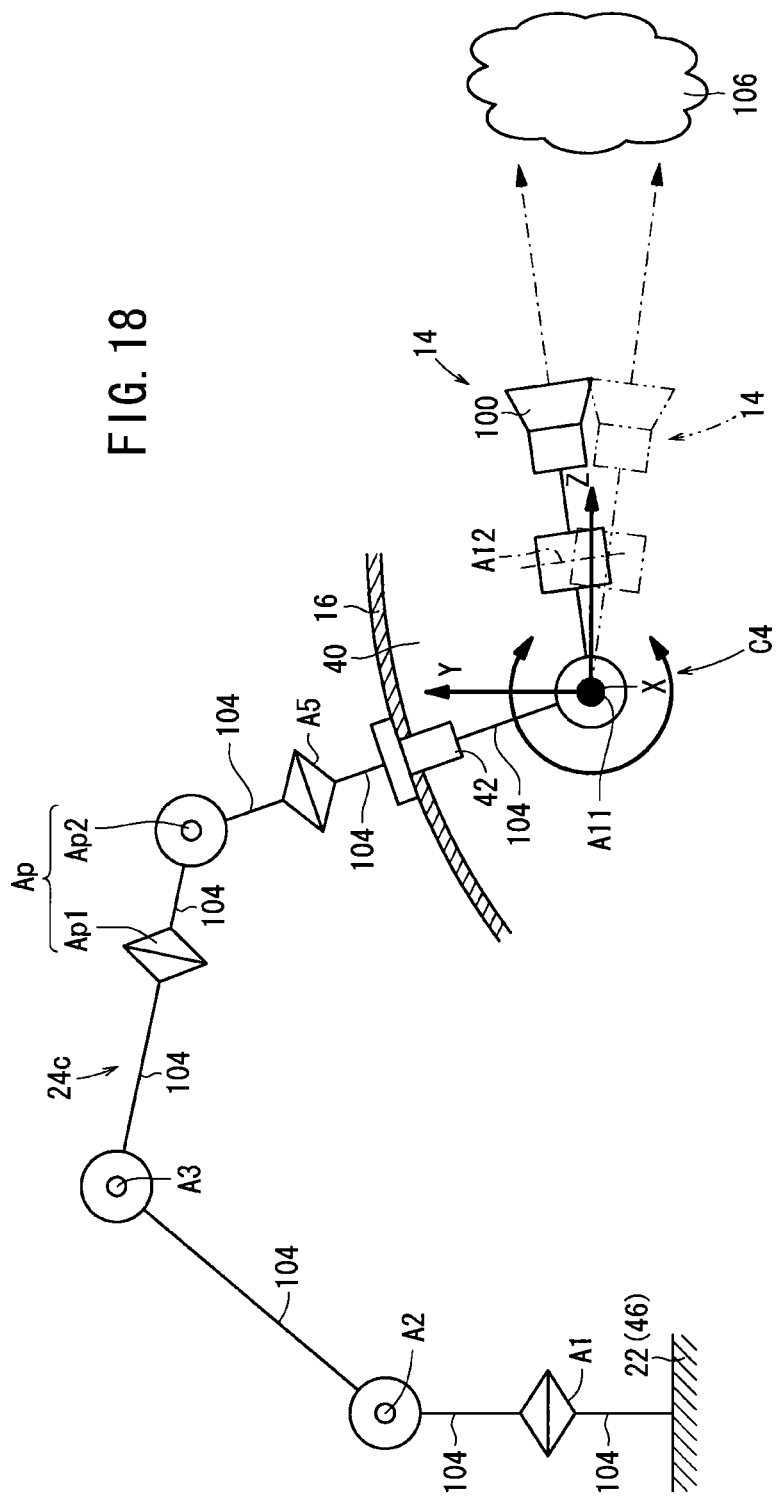
FIG. 18 illustrates a line-of-sight control in the case where an attitude coordinate system is set, in the camera arm shown in FIG. 13.

On the other hand, as shown in FIG. 18, drive control may be conducted so as to change the attitude of the endoscope 14 with reference to an attitude coordinate system C4 which is a Cartesian coordinate system having X-axis, Y-axis and Z-axis set on the first attitude rotational axis A11. In this case, during a period in which no interference avoiding motion of the camera arm 24c is carried out, for example, if it is desired to change the visual field inside the body cavity 40, the visual field can be changed and a broader area can be viewed by merely controlling the rotation of the first attitude rotational axis A11 of the endoscope 14 or the like, without need to drive the camera arm 24c.

Thus, even in the camera arm 24d (24e) lacking the redundant degree of freedom, when the line-of-view of the endoscope 14 is guided by controlling the rotation of the attitude axes (A11 to A14) of the endoscope 14 including at least two rotational axes with reference to a predetermined coordinate system, it is possible to carry out an interference avoiding motion while keeping constant the visual point of the endoscope 14. Naturally, the line-of-view control of the endoscope 14 based on any of the coordinate systems as shown in FIGS. 15 to 18 may be carried out during a surgical operation while changing the coordinate system by setting changing switches or the like (not shown) provided on the console 26 side.

The present invention is not limited to the above-described embodiments, and, naturally, various configurations are possible without departing from the scope of the invention.

What is claimed is:

1. A medical robot system, comprising:
   a forceps arm including a forceps manipulator at the distal end thereof;
   a camera arm including an endoscope at the distal end thereof, the forceps manipulator and the endoscope being insertable into a living body through a common insertion implement, wherein the camera arm has a multiaxial joint mechanism having a redundant degree of freedom, the camera arm being configured to provide a redundant degree of freedom of movement for the endoscope;
   an operating unit operable by an operator and configured to generate a control signal to control the forceps manipulator and the forceps arm;
   a forceps motion control unit configured to control motions of the forceps manipulator and the forceps arm according to the control signal generated by the operating unit;
   an endoscope motion control unit configured to control motions of the endoscope and the camera arm; and
   an interference avoiding unit configured to provide an interference avoiding motion of the camera arm to avoid interference between the camera arm and the forceps arm within the common insertion implement, the interference avoiding unit configured to calculate an interference avoiding position and a region expected to be occupied by the camera arm at the interference avoiding position, the interference avoiding unit determining whether it is possible or impossible to avoid interference of the camera arm with the forceps arm by moving the camera arm into the region excepted to be occupied, and calculating a trajectory along which the camera arm is to be moved to the interference avoiding position when there is a risk of interference between the forceps arm and the camera arm, wherein the interference avoiding motion is performed such that a visual point of the endoscope, when the endoscope is inserted into the living body through the common insertion implement, is kept substantially constant, and wherein the endoscope motion control unit moves the camera arm along the trajectory calculated by the interference avoiding unit when there is a risk of interference between the forceps arm and the camera arm.

2. The medical robot system of claim 1, wherein the forceps motion control unit includes a first calculation unit configured to calculate a first region to be occupied by the forceps arm, and the endoscope motion control unit includes a second calculation unit configured to calculate a second region to be occupied by the camera arm, the medical robot system further comprising:
a risk determination unit configured to determine the risk of interference between the forceps arm and the camera arm according to the first and second regions calculated by the first calculation unit and the second calculation unit, wherein the trajectory for the interference avoiding motion of the camera arm is calculated when the risk determination unit determines that there is the risk of interference.

3. The medical robot system of claim 2, wherein the risk determination unit determines the risk of interference between the forceps arm and the camera arm based on a risk of interference for upper end portions of those arm members of the forceps arm and the camera arm which are provided approximately along a straight line through the insertion implement.

4. The medical robot system of claim 3, wherein the cam a arm is configured to provide at least six degrees of freedom of movement for the endoscope.

5. The medical robot system of claim 1, wherein the endoscope has an attitude change axis at a part which is inserted through the insertion implement and disposed inside the living body, an attitude of the endoscope being changeable around the attitude change axis.

6. The medical robot system of claim 5, wherein the endoscope motion control unit controls the attitude of the endoscope around the attitude change axis with reference to an organ coordinate system set at a patients organ or an offset coordinate system set with an offset from the organ, thereby keeping constant the visual point of the endoscope during the interference avoiding motion.

7. The medical robot system of claim 1, further comprising: a visual point fixation switch operable by the operator to determine whether to keep constant the visual point of the endoscope; wherein the endoscope motion control unit performs a control to keep substantially constant the visual point of the endoscope, during the interference avoiding motion of the camera arm relative to the forceps arm, only in the case where the visual point fixation switch is set to keep substantially constant the visual point of the endoscope.

8. The medical robot system of claim 1, wherein the camera arm is configured to provide at least six degrees of freedom of movement for the endoscope.

9. The medical robot system of claim 1, wherein the camera arm is configured to provide at least seven degrees of freedom of movement for the endoscope.

10. A medical robot system, comprising;
a forceps arm including a forceps manipulator at the distal end thereof;
a camera arm including an endoscope at the distal end thereof, the forceps manipulator and the endoscope being insertable into a living body through a common insertion implement, wherein the camera arm has a multiaxial joint mechanism having a redundant degree of freedom, the camera arm being configured to provide a redundant degree of freedom of movement for the endoscope;
operating means for generating a control signal to control the forceps manipulator and the forceps arm;
forceps motion control means for controlling motions of the forceps manipulator and the forceps arm according to the control signal generated by the operating means;
endoscope motion control means for controlling motions of the endoscope and the camera arm; and
interference avoiding means for controlling an interference avoiding motion of the camera arm to avoid interference between the camera arm and the forceps arm within the common insertion implement, the interference avoiding motion being performed such that a visual point of the endoscope, when the endoscope is inserted into the living body through the common insertion implement is kept substantially constant, the interference avoiding means configured to calculate an interference avoiding position and a region expected to be occupied by the camera arm at the interference avoiding position,
the interference avoiding means determining whether it is possible or impossible to avoid interference of the camera arm with the forceps arm by moving the camera arm into the region expected to be occupied, and calculating a trajectory along which the camera arm is to be moved to the interference avoiding position when there is a risk of interference between the forceps arm and the camera arm,
wherein the endoscope motion control means moves the camera arm along a trajectory calculated by the interference avoiding means when there is a risk of interference between the forceps arm and the camera arm.

11. The medical robot system of claim 10, to provide at least seven degrees of freedom of movement for the endoscope.

12. A medical robot system, comprising:
a first arm of a multi-axis configuration for multi-axial movements;
a forceps unit removably attached to the first arm at the distal end thereof;
a second arm of a multi-axis configuration for multi-axial movements;
an endoscope removably attached to the second arm at the distal end thereof, the distal end of the endoscope being controllable to move, and the forceps unit and the endoscope being inserted into a living body through a common insertion implement, wherein the second arm has a multiaxial joint mechanism having a redundant degree of freedom, the second arm being configured to provide a redundant degree of freedom of movement for the endoscope;

an operating unit operable by an operator and configured to generate a control signal to control the first arm, the second arm, the forceps unit and the endoscope;

a first control unit configured to control motions of the first arm and the forceps unit according to the control signal generated by the operating unit;

a second control unit configured to control motions of the second arm and the endoscope according to the control signal generated by the operating unit; and an interference avoiding unit configured to control the motions of the first arm and/or second arm to avoid interference between the first arm and the second arm within the common insertion implement, a visual point of the endoscope, when the endoscope is inserted into the living body through the common insertion implement, being kept substantially constant while the interference avoiding unit controls the motion of the first arm and/or the second arm, the interference avoiding unit configured to calculate an interference avoiding position and a region expected to be occupied by the first arm at the interference avoiding position, the interference avoiding unit determining whether it is possible or impossible to avoid interference of the first arm with the forceps unit by moving the first arm into the region excepted to be occupied, and calculating a trajectory along which the first arm is to be moved to the interference avoiding position when there is a risk of interference between the first arm and the second arm, wherein the endoscope motion control unit moves the second arm along the trajectory calculated by the interference avoiding unit when there is a risk of interference between the forceps arm and the second arm.

13. The medical robot system of claim 12, to provide at least six degrees of freedom of movement for the endoscope.

14. The medical robot system of claim 12, to provide at least seven degrees of freedom of movement for the endoscope.

* * * * *